United States Patent [19]
Schröder

[11] Patent Number: 4,608,054
[45] Date of Patent: Aug. 26, 1986

[54] ADJUSTABLE CONNECTION FOR CONNECTING ADJOINING PARTS OF AN ARTIFICIAL LIMB

[75] Inventor: Mats Schröder, Stockholm, Sweden

[73] Assignee: Landstingens Inkopscentral LIC, Sweden

[21] Appl. No.: 620,431

[22] Filed: Jun. 14, 1984

[30] Foreign Application Priority Data

Jun. 15, 1983 [SE] Sweden ............................. 8303415

[51] Int. Cl.⁴ .................................................. A61F 2/64
[52] U.S. Cl. ........................................ 623/39; 623/28; 623/27
[58] Field of Search ................... 3/1.911, 22, 17 R, 31; 403/115, 122, 362; 623/20, 39, 27

[56] References Cited

U.S. PATENT DOCUMENTS

| | | | |
|---|---|---|---|
| 3,790,965 | 2/1974 | Gelbenegger | 3/22 X |
| 3,885,252 | 5/1975 | Nakajima | 623/39 X |
| 4,312,081 | 1/1982 | Munny | 623/39 |
| 4,379,350 | 4/1983 | Munny | 623/39 |
| 4,458,367 | 7/1984 | May | 623/39 |

FOREIGN PATENT DOCUMENTS 2410998  7/1979  France .
360257  9/1973  Sweden .

*Primary Examiner*—Richard J. Apley
*Assistant Examiner*—Alan W. Cannon
*Attorney, Agent, or Firm*—Ostrolenk, Faber, Gerb & Soffen

[57] ABSTRACT

An adjustable connection for adjoining parts of an artificial limb comprises a first and a second coupling element, each of which forms part of or is intended to be fixed to a respective one of the aforementioned artificial-limb parts to be connected together. The adjustable connection includes set screws which are intended to hold the coupling elements, and therewith the artificial-limb parts releasably in desired positions relative to one another. The coupling elements have centrally located, mutually coacting support surfaces, and the set screws are arranged in an outer annular flange which depends from one coupling element and encircles the other coupling element with a clearance between the elements, and which has an unloaded annular edge.

22 Claims, 6 Drawing Figures

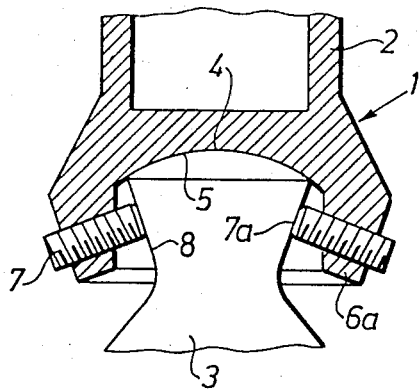
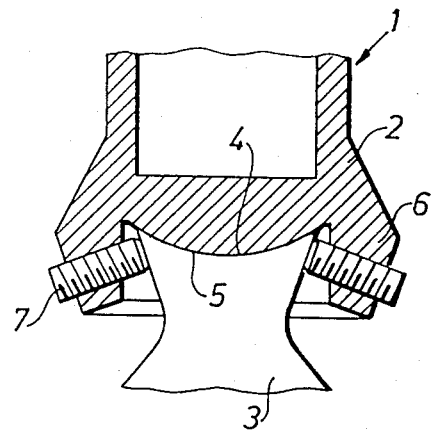
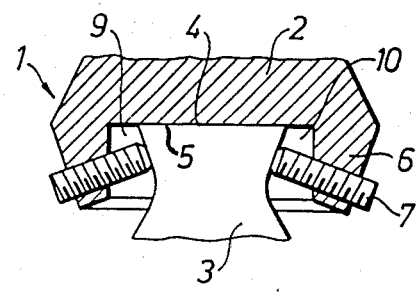
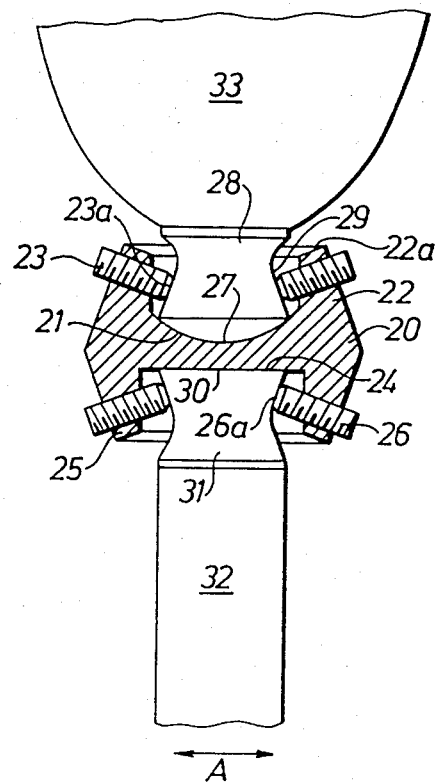

ADJUSTABLE CONNECTION FOR CONNECTING ADJOINING PARTS OF AN ARTIFICIAL LIMB

FIELD OF THE INVENTION

The present invention relates to an adjustable connection for connecting adjoining parts of an artificial limb, whereby such parts can be fixed in desired positions relative to one another.

Prior known adjustable connections for this purpose commonly use a ball-coupling arrangement and require to be of a heavy construction in order to achieve the required strength and stability of setting in use. The resultant weight however, is quite troublesome to the wearer of the limb. In addition such known adjustable connections are in most cases also relatively bulky, and thus unattractive from a cosmetic point of view and often require, after initial setting, a subsequent final adjustment, which can be difficult to carry out.

An object of the present invention is to provide an adjustable connection of the character referred to which, in comparison to known connections can be made relatively light in weight, and which in spite of its low weight can have the necessary strength and stability of setting, can readily be adjusted to an appropriate setting, and will, after initial setting, require a minimum of subsequent adjustment.

SUMMARY OF THE INVENTION

According to one aspect of the invention, there is provided an adjustable connection for connecting adjoining parts of an artificial limb, and comprising a first and a second coupling element, said first coupling element providing a support surface and an annular flange encircling the area of said support surface and said second coupling element extending with clearance within said annular flange and having a support surface abutting said support surface of the first element, said second element being located in position within said annular flange by setting elements extending from said annular flange inwardly to engage said second element.

The coupling elements are preferably made of a lightweight metal, such as aluminium, thereby enabling the cooperating support surfaces to be given relatively large dimensions while keeping the overall weight of the construction relatively low.

The abutting central support surfaces of said coupling elements may be substantially planar, so as to enable a lateral adjustment of the elements relative to one another, parallel with the plane of the support surfaces.

Alternatively the support surface of one coupling element may be convex or concave, and the abutting support surface of the adjoining coupling element correspondingly concave or convex.

According to another aspect of the invention, there is provided an adjustable connection for connecting adjoining parts of an artificial limb, and comprising a first, a second and a third coupling element, said third coupling element being disposed between said first and second coupling elements and having a first support surface and a first annular flange encircling the area of said first support surface, said third coupling element having a second support surface directed oppositely to said first support surface and a second annular flange encircling the area of said second support surface, said first coupling element extending with clearance within said first annular flange and having a support surface abutting said first support surface, first setting elements extending inwardly from said first annular flange to engage said first coupling element and locate the same in position in the third coupling element, said second coupling element extending with clearance within said second annular flange and having a support surface abutting said second support surface, and second setting elements extending inwardly from said second annular flange to engage said second coupling element and locate the same in position in the third coupling element.

In a preferred embodiment of the invention, in this aspect, one support surface of the third coupling element may be concave or convex, while the other support surface of the third coupling element may be substantially flat, with the cooperating support surfaces of the first and second coupling elements being of complementary form.

With a connection of the last-noted design, it is possible to make both the requisite angular adjustments and the requisite lateral adjustments between the parts of an artificial limb connected by the connection all with a connecting means of extremely low weight. One important advantage afforded by a connection of the last-noted form is that the overall adjustments can be achieved with a single connecting means. A further advantage is that the separate angle adjusting means provided on the foot part of known, previous arrangements can be eliminated. These known separate adjusting means have been particularly troublesome to the wearers of such previous artificial limbs from the aspect of weight.

The abutting support surfaces may be formed so as to cooperate with one another without central contact. For example, to this end the support surface of at least one coupling element may be provided with a central, substantially planar part, or with a central aperture or recess. Such a design, together with a partial hollowing of the coupling element, will not only further reduce the weight of the connecting means, but also eliminate the risk of single-point contact between the support surfaces as a result of possible tolerances or like variations introduced in the manufacture of the connecting means.

The side surfaces of each coupling element intended for cooperation with the setting elements are suitably inclined, i.e. arranged to converge in a direction away from the respective support surface. This inclination of the side surfaces affords good stability and rigidity to the construction proposed. If the side surfaces were arranged to diverge in a direction away from the respective support surface, this would result in unfavourable fracture stresses at the junction between the side surfaces and support surface.

Embodiments of the invention are described below with reference to the accompanying drawings.

DESCRIPTION OF THE DRAWINGS

In the drawings:

FIG. 1 is a fragmentary sectional view of a first embodiment of the invention;

FIG. 2 is a fragmentary sectional view of a second embodiment of the invention;

FIG. 3 is a fragmentary sectional view of a third embodiment of the invention;

FIG. 4 is a fragmentary sectional view of a fourth embodiment of the invention;

DESCRIPTION OF EMBODIMENTS

Figure 5:
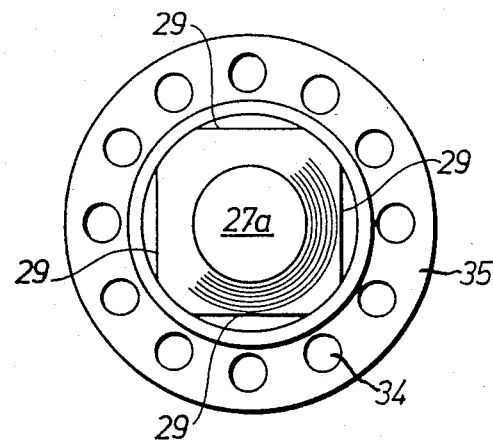
FIG. 5 is a top plan view of one coupling element of an adjustable connection embodying the invention.

An adjustable connection embodying the invention is generally designated as 1 in each of FIGS. 1-3 and in these figures, the connection comprises a first coupling element (female element) 2 and a second coupling element (male element) 3, said elements having mutually abutting first and second support surfaces 4 and 5 respectively, arranged centrally thereon. The first coupling element 2 in each of the embodiments of FIGS. 1 to 3 is provided with an outer annular flange or skirt 6. Arranged in the flange 6 is a number, suitably four, of setting elements 7, which may, for example, have the form of externally adjustable set screws.

Extending downwardly away from the support surface 5 on the coupling element 3 is a number of inclined side surfaces 8, a respective said side surface being provided for, and being engaged by, each set screw 7. These side surfaces are inclined, i.e. converge in a direction away from the support surface 5 of the coupling element 3, and the set screws 7 mounted on the annular flange engage the respective said side surfaces approximately at right angles thereto, so as to hold the two coupling elements 2, 3 in desired angular positions relative to one another.

Thus the annular flange or skirt 6 surrounds the second coupling element 3 so as to leave a clearance between the side surfaces 8 of the coupling element and the flange, and so that the free edge 6a of said annular flange does not bear against the second coupling element 3. In earlier constructions, set screws have been arranged in a coupling-element part which is subjected to load, i.e. in the close proximity of the support surface of said coupling element. In the construction proposed herein, the front edge 6a of the annular flange 6 does not serve as a support surface and is consequently not subjected to any load at all, i.e. it is un-loaded.

A further advantage afforded by the connecting means proposed herein is that it can be made of lightweight metal and can subsequently be given relatively large mutually cooperating surfaces, while obtaining a construction which is much lighter in weight than earlier known constructions. It should be mentioned in this connection that by means of the present invention it is possible to manufacture highly stable and robust connecting means of the aforesaid kind and to greatly reduce the weight of the connecting means overall. For example, compared with known constructions, a weight reduction of up to 25% can be achieved when using a connecting means according to the invention.

It will be appreciated that in the embodiments of FIGS. 1 to 3, the elements 2, 3 may comprise major parts, in the sense of being parts of major extent, of the respective artificial limbs, of which only the respective adjoining end parts are shown. Alternatively, the elements 2, 3 or one or other of these, may comprise relatively small fittings adapted to be secured, by means not shown, to such major parts.

In the embodiment of FIG. 1, the support surface 4 of the first coupling element is of concave part-spherical form and is arranged to lie over a greater part of its area against the support surface 5 of the second coupling element 3, said support surface 5 having a corresponding part-spherical convex shape.

In the embodiment of FIG. 2, the coupling element 2 bearing the annular flange or skirt 6 has a centrally located convex, part-spherical support surface 4 which is arranged to co-act with a complementary part-spherical concave support surface 5 on the second coupling element.

FIG. 3 illustrates a further embodiment of the invention in which the respective support surfaces 4, 5 of the two coupling elements 2, 3 are substantially planar.

As will also be seen from FIGS. 1 and 2, the coupling-element support surface 4 of the element carrying the annular flange 6 is always slightly larger than the corresponding coupling-element support surface 5 with which it co-acts.

The arrangements of FIGS. 1 and 2 allow the two coupling elements 2 and 3, and the associated limb parts to be adjusted in a combined translatory and pivotal sense, in the plane of the drawings, relative to one another.

The arrangement of FIG. 3 allows the two coupling elements, and therewith the associated limb parts, to be readily adjusted laterally relative to one another, without consequent pivotal movement.

As will be understood, the extent to which adjusting movement can be achieved in FIGS. 1 to 3 is influenced by the lateral clearances between the two coupling elements, said clearances being identified by references 9 and 10 in FIG. 3. It will be appreciated that adjustment of the relative positions of the elements 2, 3 in the embodiments described is effected by unscrewing the screws 7 on the side or sides to which the element 3 is to be moved and screwing up the screws 7 on the opposite side or sides.

In FIG. 4 there is illustrated another embodiment of the invention, in which the features of the embodiments of FIGS. 1 and 2 allowing relative pivotal adjustment have been combined with the features of the embodiment of FIG. 3 allowing pure translational adjustment. In the embodiment of FIG. 4, a third upper coupling element 28 and a second, lower coupling element 31 are connected via a third coupling element 20 located between elements 28 and 31 and cooperating with both of these. The coupling element 20 is provided with two oppositely facing support surfaces, i.e. an upper, concave, part-spherical support surface 21 around which extends an upwardly projecting, outer annular fange or skirt 22 of the element 20, which flange 22 carries set screws 23, and a lower, central and substantially planar support surface 24 around which extends a downwardly depending annular flange or skirt 25 carrying set screws 26. In this case, the upper central support surface 21 of the coupling element 20 is arranged to co-act with a complementary central, convex part-spherical support surface 27 provided at the lower end of the third coupling element 28 which has inclined side surfaces 29, i.e. surfaces which converge in the direction away from said support surface 27, which are arranged to co-act with the inner end surfaces 23a of the set screws 23, so as to hold the element 28 in the desired position relative to the element 20, in the same way that the element 3 is held in position in the element 2 in the embodiment of FIG. 1. Thus it is possible to hold the coupling element 28, and therewith the associated part 33 of the artificial limb, in a selected angular position relative to the elements 20 and 31 and limb part 32 fixed to element 31. The annular flange or skirt 22 encircles said coupling element 28 in a manner to leave a clearance therebetween, and so that there is no contact between the free edge 22a of the annular flange 22 and said coupling element 28, as in the embodiment of FIG. 1.

The lower, central support surface 24 of the coupling element 20 is arranged to co-act with a substantially planar, central support surface 30 of the coupling element 31, which is joined to a further part 32 of the artificial limb. The inner end surfaces 26a of the set screws 26 are intended to be brought into engagement with respective side surfaces of the coupling element 31, so as to hold the artificial-limb part 32 adjustably in a desired position. Thus, this embodiment provides for a certain amount of lateral adjusting movement of the artificial-limb part 32 relative to the part 33 along the support surface 24, as indicated by the double-headed arrow A in FIG. 4, independently of any pivotal adjustment between parts 32 and 33.

The flange 25 encircles the coupling element 31 so as to leave a clearance between flange 25 and element 31 and there is no contact between the free edge of flange 25 and element 31.

Figure 6:
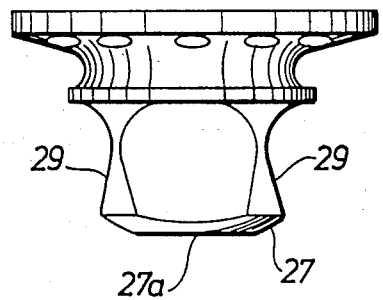
FIG. 6 is a side view of the coupling element illustrated in FIG. 5.

FIG. 5 is a top plan view of a coupling element, similar to the coupling element 28 of FIG. 4, while FIG. 6 illustrates the coupling element in side view. The illustrated coupling element has an upper flange 35 which has apertures 34 provided therein and which is intended to be firmly embedded in a part of an artificial limb such as the part 33 illustrated in FIG. 4. The actual support surface 27 is convexly part-spherical in shape and has the form of an annular ring encircling a central, substantially planar centre part 27a. Four side surfaces 29, intended for co-action with the inner ends 23a of the set screws 23, converge in a direction away from the support surface 27. This coupling element may be hollow and, as will be understood, the illustrated central part 27a may be removed entirely, thereby to reduce the weight of the element still further without detracting from the function of said element.

It will be understood that the invention is not limited to the illustrated embodiments, but that modifications can be made within the scope of the following claims. For example, the central support surfaces 24 and 21 of the coupling element 20 of the FIG. 4 embodiment may be concave or convex, or convex and substantially planar in shape, and in such cases co-act with correspondingly shaped support surfaces of co-acting coupling elements.

I claim:

1. An adjustable connection for connecting adjoining parts of an artificial limb, and comprising a first and a second coupling element, said first coupling element providing a support surface which is across the axis of said artificial limb and an annular flange encircling the area of said support surface and said second coupling element extending with clearance within said annular flange and having a support surface abutting said support surface of the first element, said second element being located in position within said annular flange by setting elements extending from said annular flange inwardly to engage said second element the flange having an annular edge and said edge being unloaded.

2. An adjustable connection according to claim 1, in which the abutting support surfaces of the coupling elements are of substantially planar configuration.

3. An adjustable connection according to claim 1, in which the support surface of the first coupling element is convex and the support surface of the second coupling element is of complementary concave form.

4. An adjustable connection according to claim 1 in which the support surface of the first coupling element is concave and the support surface of the second coupling element is of complementary convex shape.

5. An adjustable connection according to claim 1 in which the support surface of the first coupling element carrying the annular flange is larger than the support surface of the second coupling element which abuts said support surface of the first coupling element.

6. An adjustable connection for connecting adjoining parts of an artificial limb, and comprising a first, second and a third coupling element, said first coupling element being disposed between said third and second coupling elements and having a first support surface which is across the axis of said artificial limb and a first annular flange encircling the area of said first support surface, said first coupling element having a second support surface directed oppositely to said first support surface and a second annular flange encircling the area of said second support surface, said third coupling element extending with clearance within said first annular flange and having a support surface abutting said first support surface, first setting elements extending inwardly from said first annular flange to engage said first coupling element, said second coupling element extending with clearance within said second annular flange and having a support surface abutting said second support surface, and second setting elements extending inwardly from said second annular flange to engage said second coupling element and locate the same in position in the first coupling element, each of said flanges having an annular edge and each said edge being unloaded.

7. An adjustable connection according to claim 6, in which said first support surface of the first coupling element is concave and in which the second support surface of the first coupling element is substantially of planar configuration.

8. An adjustable connection according to claim 6 in which said first support surface of the third coupling element is convex and in which the second support surface of the third coupling element is substantially of planar configuration.

9. An adjustable connection according to claim 1, in which said support surfaces which abut one another encircle a central area over which the first and second elements are out of contact.

10. An adjustable connection according to claim 6 in which a portion of at least one of said support surfaces of said first connecting element is contoured so as to form a flange adjacent an abutting support surface of an adjoining element which encircles a central area over which the first element and the adjoining element are not in contact.

11. An adjustable connection according to claim 9, in which at least one of the cooperating support surfaces is provided with a centrally located, substantially planar portion.

12. An adjustable connection according to claim 10 in which at least one of the cooperating support surfaces is provided with a centrally located, substantially planar portion.

13. An adjustable connection according to claim 9, in which at least one of the cooperating support surfaces is provided with a centrally located aperture or recess.

14. An adjustable connection according to claim 10 in which at least one of the cooperating support surfaces is provided with a centrally located aperture or recess.

15. An adjustable connection according to claim 1 or claim 6 in which at least one of the coupling elements is substantially hollow, in order to reduce weight.

16. An adjustable connection according to claim 1 wherein said second coupling element has side surfaces, extending away from said support surface thereof, and which are engaged by said setting elements, said side surfaces converging in the direction away from said support surface of said second coupling element.

17. An adjustable connection according to claim 6, wherein, at least one of said coupling elements which engages said first coupling element has side surfaces extending away from said support surface thereof, and which side surfaces are engaged by the respective said setting elements, said side surfaces converging in the direction away from said support surface of said second coupling element.

18. A adjustable connection according to claim 16 or claim 17 in which said side surfaces are substantially planar.

19. An adjustable connection according to claim 16 or claim 17 in which said side surfaces are concave.

20. A connecting means according to claim 16 or claim 17 in which said side surfaces and said setting elements are so arranged that said setting elements lie substantially perpendicular to said side surfaces.

21. A connecting means according to claim 1 or claim 6 in which the setting elements are set screws.

22. An adjustable connection according to claim 1 or claim 6 wherein said setting elements engage said coupling elements so as to prohibit said coupling elements from disengaging from each other.

* * * * *